United States Patent
Adam et al.

(10) Patent No.: US 6,419,483 B1
(45) Date of Patent: Jul. 16, 2002

(54) METHOD AND APPARATUS FOR CURLING LIGHT-CURABLE DENTAL MATERIALS

(75) Inventors: Randall E. Adam, Sierra Madre, CA (US); Barbara A. DeBaun, Woodbury, MN (US); Brian W. Lotte, Hermosa Beach, CA (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 09/516,282

(22) Filed: Mar. 1, 2000

(51) Int. Cl.⁷ .................................................. A61C 1/00
(52) U.S. Cl. ......................................... 433/29; 433/215
(58) Field of Search .......................... 433/29, 215, 226, 433/229; 362/119, 120

(56) References Cited

U.S. PATENT DOCUMENTS

| | | | |
|---|---|---|---|
| 2,803,522 A | 8/1957 | Stedman | |
| 3,022,178 A | 2/1962 | Park et al. | |
| 3,075,228 A | 1/1963 | Elias | |
| 3,212,909 A | 10/1965 | Leigh | |
| 3,819,522 A | 6/1974 | Zmoda et al. | |
| 3,897,356 A | 7/1975 | Pociluyko | |
| 3,949,477 A | 4/1976 | Cohen et al. | |
| 4,385,344 A | 5/1983 | Gonser | |
| 4,478,909 A | 10/1984 | Taniguchi et al. | |
| 4,619,612 A | * 10/1986 | Weber et al. | 433/29 |
| 4,888,489 A | 12/1989 | Bryan | |

(List continued on next page.)

FOREIGN PATENT DOCUMENTS

| | | |
|---|---|---|
| CA | 2106020 | 3/1995 |
| DE | 295 11 927 | 2/1997 |
| EP | 0780103 | 6/1997 |
| EP | 0780104 | 6/1997 |
| FR | 2344785 | 10/1977 |
| JP | 8141001 | 6/1996 |
| JP | 97010238 | 1/1997 |
| WO | WO 95/07731 | 3/1995 |
| WO | WO 96/18691 | 6/1996 |
| WO | WO 99/2267 | 5/1999 |
| WO | WO 99/23968 | 5/1999 |
| WO | WO 99/36248 | 7/1999 |
| WO | WO 99/36258 | 7/1999 |
| WO | WO 99/36809 | 7/1999 |
| WO | WO 99/36810 | 7/1999 |
| WO | WO 00/07044 | 2/2000 |
| WO | WO 00/07046 | 2/2000 |
| WO | WO 00/07068 | 2/2000 |
| WO | WO 99/07043 | 2/2000 |

OTHER PUBLICATIONS

Hewlett Packard; High–Flux LED Blue, Green and Bluish –Green; Preliminary Technical Data, 6 pages, copyright 1999.

Hewlett Packard; LED Light Source Design Guide, Preliminary, Feb. 3, 1999, pp. 1–15.

CREE, G–Sic Technology, Super Bright LEDs, CXXX–C290–E1000, 4 pages, May 1999.

*Primary Examiner*—Todd E. Manahan
(74) *Attorney, Agent, or Firm*—James D. Christoff (57) ABSTRACT

A method and apparatus for curing photocurable dental materials involve a solid state light emitter and a source of electrical current connected to the light emitter. The source of electrical current provides a current to the light emitter that is sufficient to reduce the lifetime of the light emitter to less than 10 hours. The intensity of light from the light emitter is substantially increased and the apparatus can be conveniently disposed of after use on a single patient. A light guide that includes two conical optical surfaces collects light from the solid state light emitter and optionally directs the light to a third optical surface which has the shape of an elongated, curved tube.

31 Claims, 4 Drawing Sheets

U.S. PATENT DOCUMENTS

| | | |
|---|---|---|
| 5,003,434 A | 3/1991 | Gonser et al. |
| 5,030,093 A | 7/1991 | Mitnick |
| 5,049,068 A | 9/1991 | Sterrett et al. |
| 5,147,204 A | 9/1992 | Patten et al. |
| 5,184,044 A | 2/1993 | Thomas |
| 5,316,473 A | 5/1994 | Hare |
| 5,328,363 A | 7/1994 | Chester et al. |
| 5,420,768 A | 5/1995 | Kennedy |
| 5,487,662 A | 1/1996 | Kipke et al. |
| 5,575,645 A | 11/1996 | Jacobs et al. |
| 5,634,711 A * | 6/1997 | Kennedy et al. ............. 433/29 |
| 5,711,665 A | 1/1998 | Adam et al. |
| 5,882,774 A | 3/1999 | Jonza et al. |
| 5,971,755 A * | 10/1999 | Liebermann et al. ......... 433/29 |
| 5,975,895 A * | 11/1999 | Sullivan ...................... 433/29 |
| 6,099,520 A * | 8/2000 | Shimoji ....................... 433/29 |
| 6,102,696 A * | 8/2000 | Osterwalder et al. ......... 433/29 |
| 6,159,005 A * | 12/2000 | Herold et al. ................. 433/29 |
| 6,181,369 B1 * | 1/2001 | Ooshima et al. ............. 433/29 |
| 6,200,134 B1 * | 3/2001 | Kovac et al. ................. 433/29 |
| 6,202,242 B1 * | 3/2001 | Salmon et al. ............... 433/29 |

\* cited by examiner

METHOD AND APPARATUS FOR CURLING LIGHT-CURABLE DENTAL MATERIALS

BACKGROUND OF THE INVENTION

1. Field of the Invention

This invention broadly relates to methods and apparatus for curing light-curable dental materials such as orthodontic adhesives, dental sealants and dental restorative materials. More particularly, the present invention relates to a portable, small, hand-held curing apparatus that includes at least one solid state light emitter, and methods for using that apparatus.

2. Description of the Related Art

A wide variety of curable materials are used in the field of dentistry. Typical examples include restorative materials (commonly known as "fillings") and dental sealants. Other examples include various types of dental adhesives such as orthodontic adhesives. Orthodontic adhesives are often used during orthodontic treatment to bond tiny appliances known as brackets to the surfaces of teeth.

Curable dental materials are sometimes supplied as two initially separate components that self-cure once mixed together. Unfortunately, these two-component materials have only a limited "working time" during which the mixture can be placed and manipulated before the mixture begins to harden. As an example, once the components of a two-component orthodontic adhesive are mixed together, the practitioner has only a limited amount of time to transfer the adhesive to the base of the bracket, place the bracket on the tooth and then shift the bracket to a particular desired location on the tooth before the adhesive becomes stiff.

Other dental materials, however, are light-curable and begin to cure only after a source of light is directed toward the material. As can be appreciated, such light-curable materials are widely preferred because the length of the "working time" can be extended as needed. For example, light curable orthodontic adhesives enable the practitioner to take as much time as needed to carefully place the bracket on the patient's tooth and precisely shift the bracket as desired. Once the practitioner is completely satisfied with the position of the bracket on the tooth, a source of light can then be directed toward the adhesive in order to securely fix the bracket in place.

One type of dental light curing apparatus has a housing with a "pistol-grip" configuration. The housing includes a lamp (such as a halogen lamp) that is located in a central section of the housing above the handle. A light guide, often made of a bundle of optical fibers that are fused together, extends outwardly from the housing and is somewhat slender in order to fit within the oral cavity. Typically, the light guide can be swiveled about its longitudinal axis in order to facilitate positioning of the emitted light.

Examples of pistol-grip dental curing apparatus are described, for example, in U.S. Pat. Nos. 4,888,849 and 5,147,204, both of which are assigned to the assignee of the present invention. However, such light curing units are not entirely satisfactory because the housing enclosing the light is somewhat bulky and in some cases obstructs the practitioner's view of the oral cavity. Unfortunately, it is difficult to reduce the size of the housing because sufficient space must be provided to enclose the lamp as well as an adjacent fan for cooling the lamp during operation.

Recently, there has been increased interest in the use of solid state light emitters to replace the lamps used in dental curing apparatus. Solid state light emitters, such as light emitting diodes (also known as "LEDs") and laser diodes, are typically smaller than the halogen lamps mentioned above. Solid state light emitters also emit less heat than halogen lamps and as a result the need for a fan often can be avoided.

Examples of dental light emitting curing apparatus having solid state light emitters are described in U.S. Pat. Nos. 5,711,665, 5,634,711, 5,487,662 and PCT application No. WO 99/22667. The curing units described in those references are relatively small, compact, light in weight and in some instances operated using a battery. Such construction is an advantage, in that it facilitates maneuvering the apparatus in the oral cavity, a particular benefit in posterior regions of the oral cavity where access is somewhat limited. Additionally, the units are relatively quiet during operation if designed to operate without a fan or other mechanical cooling device.

However, known solid state light emitting dental curing apparatus are not favored in certain applications, because the light emitted from the apparatus has insufficient intensity to adequately cause certain dental materials to cure within a relatively short period of time. To overcome this issue, some have suggested the use of multiple numbers of solid state light emitters positioned closely together in an array. Unfortunately, when multiple solid state light emitters are employed, the power consumption of the apparatus is increased by a corresponding multiple amount, with the result that battery life of the apparatus is reduced. It is possible to increase the size of the battery or to replace the battery with a transformer, rectifier and power cord for connection to a source of A.C. line voltage, but those options hinder maneuverability of the device in use.

High intensity curing units have also been suggested in the past. One example of a commercially available high intensity curing apparatus is known as "Apollo 95E" from Dental/Medical Diagnostics of Woodland Hills, Calif., and has a xenon bulb that provides plasma arc light. Another example of a high intensity dental light curing apparatus is known as "LaserMed AccuCure 3000" from LaserMed of Salt Lake City, Utah, and has an argon laser that emits a blue light.

Conventional high intensity dental curing units, including the high intensity curing apparatus described in the preceding paragraph, are favored by some practitioners because substantially less time is needed to initiate the curing reaction in some light-curable materials. However, such curing units are relatively expensive. Furthermore, the source of light of conventional high intensity dental light curing units is typically located within a base adapted to sit on the practitioner's countertop or other surface, and a length of light guide such as a glass fiber optic cable or "liquid cable" is provided to direct the light where needed. As can be appreciated, the tethered nature of that light guide somewhat restricts maneuverability of the apparatus in use. In addition, many practitioners prefer to avoid dedicating space on the countertop in an area close to the patient's chair for the base of the unit.

There exists a need in the art for a dental light curing apparatus that can be used with a wide variety of light-curable dental materials, that is highly maneuverable, and yet functions to cure the selected dental material within a relatively short period of time.

SUMMARY OF THE INVENTION

The present invention is directed toward a method and apparatus for curing photocurable dental material that involves the use of a solid state light emitter providing greater intensity than known methods and apparatus. In particular, the invention involves overdriving a solid state light emitter to increase the intensity of the emitted light so that the dental material can cure at a faster rate. Although overdriving the solid state light emitter will substantially decrease its life, the apparatus is adapted to be disposable and used with only a single patient. As a result, the expected reduced lifetime of the emitter is not a concern.

In more detail, the invention in one aspect is directed toward a dental light curing apparatus that comprises a housing and a solid state light emitter connected to the housing. The apparatus also includes a source of electrical current connected to the solid state light emitter. A source of electrical current provides a current to the solid state light emitter that is sufficient to reduce the lifetime of the solid state emitter to less than 10 hours.

Another aspect of the invention relates to a method of bonding a quantity of photocurable dental material to a tooth. The method includes the acts of placing a quantity of photocurable material in contact with the tooth and activating a solid state light emitter in order to direct actinic radiation toward the photocurable material. The act of activating a solid state light emitter includes the act of directing an electrical current to the solid state light emitter in an amount sufficient to reduce the lifetime of the solid state light emitter to less than 10 hours.

The invention is also directed to a dental kit that comprises a container and a set of orthodontic brackets received in the container. The kit further includes a solid state light emitter that is received in the container.

The apparatus of the invention provides significant benefits when compared to other known light emitting apparatus for curing dental material. Since the solid state light emitter is overdriven and the apparatus is preferably disposed of after use with a single patient, a battery may be optionally used as a source of power for the apparatus. As such, the apparatus can be self-contained and need not be tethered to an external source of power.

Moreover, use of a solid state light emitter avoids the need for a fan or other cooling mechanism. As a consequence, the apparatus can be relatively inexpensive, compact, light in weight and quiet in operation. The apparatus is highly maneuverable, allowing the light to be directed toward essentially any region of the oral cavity as desired without unduly obstructing the practitioner's view of the area of interest.

DETAILED DESCRIPTION OF THE PREFERRED EMBODIMENTS

A dental light curing apparatus according to one embodiment of the invention is illustrated in FIGS. 1–4 and is broadly designated by the numeral 20. The apparatus 20 includes a charging stand 22 that is adapted for placement on a horizontal surface in the dental operatory or dental laboratory, such as a countertop or shelf. The charging stand 22 includes an internal battery charging circuit 24 shown schematically in (FIG. 2) that can be constructed according to any one of a number of battery charging circuits known in the art. Although not shown in the drawings, a power cord electrically coupled to the battery charger 24 leads away from the charging stand 22 for connection to a source of power, such as 110 volt A.C. line power.

The apparatus 20 also includes a housing 26 having an overall, generally cylindrical shape. A lower end portion of the housing 26 is detachably received in an upwardly-facing cylindrical receptacle 28 of the charging stand 22. Preferably, the upper end of the receptacle 28 includes a chamfered portion as shown in FIGS. 1 and 2 to facilitate guiding the lower end portion of the housing 26 in the receptacle 28 when desired.

Figures 1, 2:
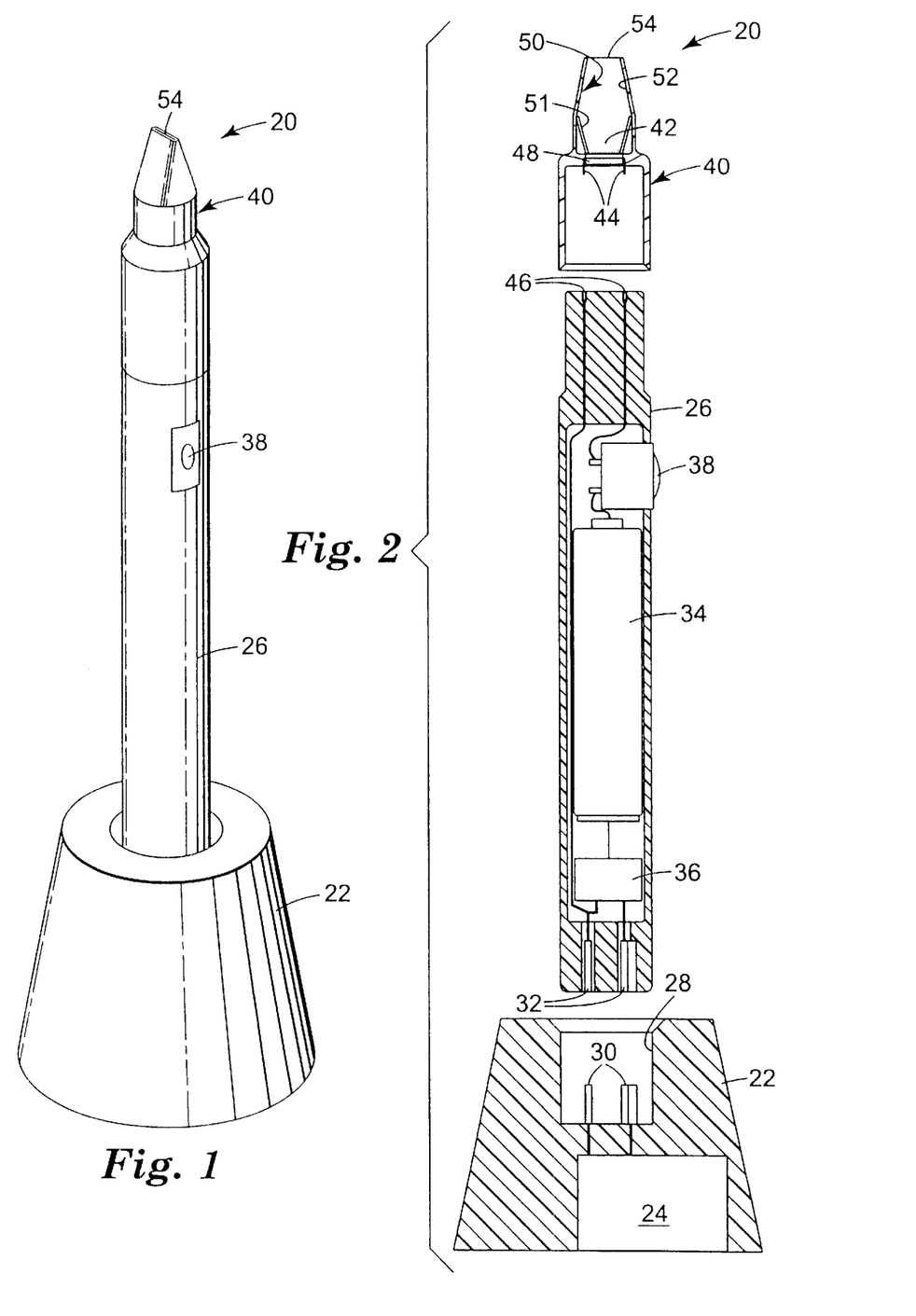
FIG. 1 is a perspective view of a dental light curing apparatus according to one embodiment of the invention.
FIG. 2 is a side cross-sectional view in exploded format of the dental light curing apparatus shown in FIG. 1.

As illustrated in FIG. 2, the charging stand 22 includes a pair of upstanding metallic prongs 30 that are electrically connected to the battery charging circuit 24. When the lower end portion of the housing 26 is received in the receptacle, the prongs 30 are respectively received in a pair of female electrical contacts 32 in order to provide power to recharge a battery 34. The battery 34 is received in a cavity of the housing 26, and is preferably rechargeable a substantial number of times.

As shown schematically in FIG. 2, the housing 26 also contains a control circuit 36 that is electrically connected to the battery 34 as well as to a switch 38. The switch 38 is mounted on a sidewall of the housing 26, and a finger-operated button of the switch 38 extends through an opening of the housing 26.

The apparatus 20 also includes a tip section 40. In the particular embodiment shown, a lower end of the tip section 40 has a hollow cylindrical configuration that is complemental to the configuration of an upper, reduced-diameter portion of the housing 26. The lower portion of the tip section 40 is detachably and matingly received on the upper portion of the housing 26, and can be separated from the housing 26 by pulling the housing 26 and the tip section 40 in opposite directions for sliding disengagement.

A middle portion of the tip section 40 carries a solid state light emitter 42. The light emitter 42 has leads that are connected to a pair of stiff electrical contacts 44. The contacts 44 depend from the middle portion of the tip section 40 in directions toward the housing 26 and parallel to a central reference axis of the tip section 40 and the housing 26. Optionally, a small circuit board may be used to mount the solid state light emitter 42 and serve as a support for the contacts 44. When the tip section 40 is received in the housing 26 as shown in FIG. 1, the electrical contacts 44 mechanically and electrically connect in respective fashion to a pair of electrical contacts 46 that are mounted on the upper end portion of the housing 26.

Figure 3:
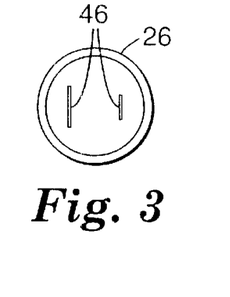
FIG. 3 is a plan view showing the upper end of a housing of the dental light curing apparatus illustrated in FIGS. 1–2.
Figure 4:
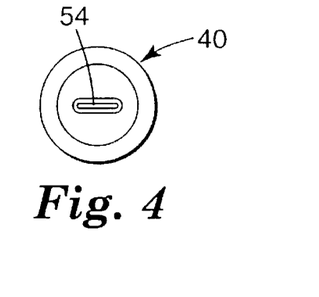
FIG. 4 is a plan view looking toward the upper end of a tip section of the dental light curing apparatus shown in FIGS. 1 and 2.

FIG. 3 illustrates the difference in width of the electrical contacts 46. The electrical contacts 44 have a similar difference in width and are adapted to mate with the electrical contacts 46 in only one rotative direction relative to the longitudinal axis of the housing 26 so that correct electrical polarity of current flowing to the light emitter 42 can be assured. Optionally, the lower portion of the tip section 40 and the upper portion of the housing 26 may have one or more keyways and mating keys for reception in the keyways in addition to or in substitution for the relative size difference of the contacts 44, 46 in order to assure that correct polarity is maintained whenever the tip section 40 is received on the housing 26.

The solid state light emitter 42 is preferably a light emitting diode or a laser diode that emits light having a wavelength suitable for photoinitiation of light-curable dental material. As used herein, the term "light" shall mean any electromagnetic radiation capable of photoinitiating a dental material. Preferably, the light shall have wavelengths in the spectrum ranging from the ultraviolet wavelengths to the infared wavelengths (including the visible wavelengths). More preferably, the light shall have a wavelength in the visible spectrum, such as a wavelength substantially in the range of about 413 nanometers to about 535 nanometers. A particularly preferred wavelength is about 470 nanometers. However, other wavelengths are also possible, and may be chosen according to the wavelength of light that best initiates the reaction of the particular dental material selected for use.

Examples of suitable blue light emitting diodes include the high-flux LED lamps from LumiLeds Lighting, U.S., LLC (Part No. HPWL-BB01) and the "SuperBright" LED lamps from Cree Research, Inc. (Part No. C470). However, other solid state light emitters may also be employed. As used herein, the phrase "solid state light emitter" means any device that converts electric energy into electromagnetic radiation through the recombination of holes and electrons. In addition to the semi-conductor light emitting diodes and semi-conductor laser diodes mentioned above, the solid state light emitters may alternatively be polymer light emitting diodes and electroluminescent devices (i.e., devices that convert electrical energy to light by a solid phosphor subjected to an alternating electric field).

Optionally, the apparatus 20 includes a heat sink 48 that is thermally coupled to the solid state light emitter 42. As one example, the heat sink 48 may be connected to the middle portion of the tip section 40 in secure mechanical and thermal contact with a rear or lower wall of the light emitter 42. Other constructions are also possible. The heat sink 48 is made of a suitable material having high thermal conductivity (such as aluminum) for quickly dissipating heat away from the light emitter 42. However, the heat sink 48 is electrically isolated from the electrical components including the contacts 44 and the leads of the solid state light emitter 42.

When the tip section 40 is received on the housing 26 in the manner shown in FIG. 1, the battery 34 and the control circuit 36 collectively provide a source of electrical current to the light emitter 42. Preferably, the electrical current provided to the light emitter 42 is sufficiently high to "overdrive" the light emitter 42, so that sufficient light flux is provided by the light emitter 42 to rapidly cure the dental material of interest.

When a solid state light emitter is overdriven, the expected lifetime of the emitter is reduced. Preferably, the source of electrical current (e.g., the battery 34) provides a current to the solid state light emitter 42 that is sufficient to reduce the lifetime of the solid state light emitter 42 to less than 10 hours. More preferably, the current that is provided to the light emitter 42 is sufficient to reduce the lifetime of the light emitter 42 to less than 2 hours, and most preferably to less than 1 hour. In this manner, a substantial flux of light is provided.

However, the magnitude of electrical current provided to the solid state light emitter 42 is not unduly high. As a result, the lifetime of the light emitter 42 is sufficient to cure all of the photocurable dental material that is expected to be encountered during the course of treatment. Preferably, the source of electrical current provided to the solid state light emitter 42 does not reduce the lifetime of the light emitter 42 to less than 10 seconds, and more preferably does not reduce to lifetime to less than 2 minutes. Preferably, the current provided to the light emitter 42 when used for orthodontic treatment enables the light emitter 42 to have a lifetime in the range of about 10 seconds to about 1 hour, more preferably in the range of about 2 minutes to about 2 hours and most preferably within the range of about 10 minutes to 1 hour. However, the preferred lifetime may change in accordance with the type of dental material chosen and the type of dental treatment desired. For example, the lifetime may be shorter when the light emitter 42 is part of a kit for restoring a tooth.

The lifetime of the light emitter 42 is typically determined by a combination of the magnitude of electrical current as well as the rate of heat dissipation away from the light emitter 42. Thus, if the optional heat sink 48 is provided and functions to effectively remove heat from the light emitter 42 during operation, the magnitude of electrical current can be somewhat higher without reducing the lifetime of the light emitter 42. However, if the heat sink 48 is omitted, the magnitude of electrical current provided to the light emitter 42 should be somewhat less so that the lifetime of the light emitter 42 is not unduly reduced.

Additionally, the wavelength of light emitter by the solid state light emitters tends to change when the emitters are overdriven. Accordingly, the selection of the light emitter 42 should take into account the amount of expected color shift, in view of the ideal wavelength for initiating the photoreaction.

Preferably, the lifetime of the light emitter 42 is sufficient to provide light to satisfactorily cure at least all of the dental material to be used with a single patient during the course of treatment. For example, if the apparatus 20 is to be used for curing bracket adhesive during orthodontic treatment, the lifetime of the light emitter 42 is sufficient to cure all of the adhesive needed to bond a complete set of orthodontic brackets to the patient's teeth. Preferably, the lifetime of the light emitter 42 is somewhat greater than that mentioned in the preceding sentence in order to ensure that the same emitter 42 can also be used to rebond brackets that unintentionally detach from the teeth during the course of treatment, along with an additional amount of lifetime as a margin of safety. Additionally, in this example, the lifetime of the light emitter 42 may also be increased in order to cure other photocurable dental materials that may be encountered during the course of orthodontic treatment, such as photo-curable dental sealants.

The tip section 40 also includes a light guide 50 that surrounds the light emitter 42 in regions above the middle portion of the tip section 40. In the embodiment shown in the drawings, the light guide 50 has a pair of optical surfaces 51, 52 each having a general shape of a truncated cone. Each of the optical surfaces 51, 52 have respective central reference axes that are preferably substantially collinear. The generally truncated conical configuration of the second optical surface 52 is oppositely oriented relative to the generally truncated conical configuration of the first optical surface 51.

The smaller end portion of the first optical surface 51 surrounds the solid state light emitter 42. The larger end portion of the first optical surface 51 is nested inside of a somewhat larger inlet end portion of the second optical surface 52. The second optical surface 52 narrows as an outlet 54 is approached.

Preferably, the second optical surface 52 is flattened as the outlet 54 is approached, such that the second optical surface 52 has a flattened oval shape in cross-sections adjacent the outlet 54 and perpendicular to the central reference axis of the second optical surface 52. The flattened oval shape of the outlet 54 enables the light guide 50 to emit light in the shape of a ribbon. Preferably, the ribbon of emitted light has a cross-sectional shape that is approximately 1 mm×5 mm. However, other shapes are also possible, such as circular cross-sectional shapes.

Light emitted in the shape of a ribbon is particularly desirable when curing orthodontic adhesive that is used for directly bonding brackets to the surfaces of the patient's teeth, especially when the brackets are made of a material that is opaque to the transmission of light emitted by the light emitter 42, such as stainless steel. The ribbon of light can then be directed toward the periphery of the base of the bracket, so that the emitted light is concentrated in a direction toward the narrow band of adhesive that lies between the periphery of the bracket base and the tooth surface. A ribbon of light having a dimension of 1 mm×5 mm is particularly desirable, in that 5 mm is often the width of the largest bracket base encountered in orthodontic treatment, and the thickness of the adhesive between the base of the bracket and the tooth is typically no greater than 1 mm.

Preferably, at least one of the optical surfaces 51, 52 provides high reflectivity of light emitted from the light emitter 42. Preferably, both of the optical surfaces 51, 52 are made of a multilayer optical film including layers of at least one strain-induced birefrigent material.

As used herein, the terms "reflection" and "reflectance" and variations thereof refer to the reflectance of light rays from a surface. Similarly, the terms "transmission" and "transmittance" and variations thereof are used herein in reference to the transmission of light through a surface, optical stack, film, etc. Except where dyes or colorants are intentionally added, the optical films preferably exhibit low or minimal absorption losses (typically less than 1% of incident light), and substantially all of the incident light that is not reflected from the surface of the optical film will be transmitted therethrough.

Optical films and methods of post-forming those optical films can be found in both International Publication Nos. WO 00/07046 titled, "POST-FORMABLE MULTILAYER OPTICAL FILMS AND METHODS OF FORMING" and in WO 00/07043, titled "POST-FORMING CONTINUOUS/DISPERSE PHASE OPTICAL BODIES", both of which are incorporated by reference herein. Dental articles having multilayer optical films are described in International Publication No. WO 00/07044, titled "DENTAL ARTICLES INCLUDING POST-FORMABLE MULTILAYER OPTICAL FILMS", which is also incorporated by reference herein.

Other multilayer optical films useful in the present invention are described in U.S. Pat. No. 5,882,774 (Jonza et al.); U.S. patent application Ser. No. 08/479,319, filed Jun. 7, 1995; U.S. patent application Ser. No. 09/006,455; and International Publication Nos. WO 99/36809, WO 99/36810, WO 99/36248, and WO 99/36258 (all of which are incorporated by reference herein). Briefly, multilayer optical films as used herein refers to optical films including at least one birefrigent material provided in layers with at least one other material such that desired strain-induced refractive index differentials are provided between the layers making up the films. The multilayer optical films preferably exhibit relatively low absorption of incident light, as well as high reflectivity for both off-axis and normal light rays.

It may be preferred that the reflective films include a plurality of layers, wherein a refractive index difference between at least two adjacent layers in a first in-plane direction is greater than or equal to a refractive index difference between the at least two adjacent layers in a second in-plane direction for the film, and further wherein the refractive index difference in the first in-plane direction is greater than a refractive index difference between the at least two adjacent layers in a third out-of-plane direction for the film.

One potential advantage of the use of multilayer optical films for the optical surfaces 51, 52 is that the wavelengths over which the multilayer optical film is reflective can be tailored to those wavelengths that are optimal for photocuring the dental material. As a result, the light guide 50 may be transmissive for light outside of the photo-curing wavelengths. One practical effect of that feature is that the practitioner may be able to see through the light guide 50 during use.

Optionally, the optical surfaces 51, 52 are provided with an anti-fogging agent. Various anti-fogging agents are known in the art which are suitable for use with the present invention. Often, such materials include substances, such as fatty acids esters, which impart hydrophobic properties to the optical surfaces 51, 52 and which promote the formation of a continuous, less opaque film of water.

Coatings which reduce the tendency for surfaces to "fog" have been reported in several patents. For example, U.S. Pat. No. 3,212,909 to Leigh discloses the use of ammonium soap, such as alkyl ammonium carboxylates in admixture with a surface active agent which is a sulfated or sulfonated fatty material, to produce a anti-fogging composition. U.S. Pat. No. 3,075,228 to Elias discloses the use of salts of sulfated alkyl aryloxypolyalkoxy alcohol, as well as alkyl-benzene sulfonates, to produce an anti-fogging article useful in cleaning and imparting anti-fogging properties to various surfaces. U.S. Pat. No. 3,819,522 to Zmoda, discloses the use of surfactant combinations comprising derivatives of decyne diol as well as surfactant mixtures which include ethoxylated alkyl sulfates in an anti-fogging window cleaner surfactant mixture. Japanese Patent Kokai No. Hei 6[1994] 41,335 discloses a clouding and drip preventive composition comprising colloidal alumina, colloidal silica and an anionic surfactant. U.S. Pat. No. 4,478,909 (Taniguchi et al) discloses a cured anti-fogging coating film which comprises polyvinyl alcohol, a finely divided silica, and an organic silicon compound, the carbon/silicon weight ratio apparently being important to the film's reported anti-fogging properties. Various surfactants, include fluorine-containing surfactants, may be used to improve the surface smoothness of the coating. Other anti-fog coatings incorporating surfactants are described in U.S. Pat. Nos. 2,803,552; 3,022,178; and 3,897,356. World Patent No. PCT 96/18,691 (Scholtz et al) discloses means by which coatings may impart both anti-fog and anti-reflective properties.

The light guide 50 may optionally be constructed of a multilayer optical film that is mounted on a substrate. The substrate may be manufactured integrally with the multilayer optical film, or alternatively may be manufactured independently and later attached to the optical film. The substrate may have an exterior surface matching the generally conical shapes of the optical surfaces 51, 52, or alternatively have a somewhat different shape such as the part-cylindrical, part-tapered shape shown in FIGS. 1–2.

If the substrate is manufactured integrally with the multilayer optical film, the substrate may be a thicker layer of one of the materials provided in the multilayer optical film, or it may be provided of another material that can be coextruded, cast or otherwise formed with the multilayer optical film. As another alternative, the substrate may be provided as a coating on the multilayer optical film. The substrate or substrates may be a single layer or a composite of different layers of the same or different materials based on the desired characteristics of the substrate.

In some cases, the materials selected for the substrate may have little, if any, effect on the optical properties of the multilayer optical film but will provide a structural layer that is otherwise compatible with the multilayer optical film. In one aspect, the substrate may simply supply desired structural stiffness/rigidity to the article, thereby reducing the need to laminate the multilayer optical film to another structure. Examples of suitable materials for the substrate include, but are not limited to polycarbonates, polyvinyl chlorides, PETG, acrylics, methacrylics, nylons, polyolefin, polypropylene, etc.

Another mechanical property that may be supplied by the substrate is strain-hardening during deformation as discussed above with respect to the multilayer optical film. That strain-hardening property may be used to limit the stresses placed on the attached multilayer optical film, thereby acting to distribute the stresses over the multilayer optical film.

The materials selected for substrate may provide desired optical properties instead of, or in addition to, desired mechanical properties. For example, the substrate may prevent or reduce transmission of selected wavelengths of light such as infrared radiation, the substrate may include colorants or otherwise introduce color into restorative material and/or the substrate may provide diffusing properties in either or both transmittance or reflectance.

Although in many instances the substrate will be coextensive with the multilayer optical film, it is also envisioned that the substrate may be attached only on selected areas of the multilayer optical film. It will also be understood that the substrate may be provided in the form of a grid, mesh or other discontinuous form on the multilayer optical film.

A number of alternative constructions are also possible. For example, a heat sink may be located on the outer, upper end of the housing 26, such that when the tip section 40 is placed on the housing 26 the heat sink contacts the solid state light emitter 42. In that instance, the heat sink 48 is omitted. As another alternative, the heat sink 48 carried by the tip section 40 is arranged to contact a second heat sink that is located on the upper end of the housing 26 when the tip section 40 is assembled to the housing 26.

As an option, the apparatus 20 may include an indicator that provides an audible signal that can be heard whenever the light emitter 42 is emitting light, or that can be heard at pre-determined intervals of time (for example, a short beep that can be heard every 10 seconds). Other types of indicators include small digital or analog meters that indicate the strength of the light emitted from the light emitter 42, and also vibratory mechanisms. Providing signals at predetermined time intervals advantageously enables the practitioner to determine the length of time that the photocurable dental material has been exposed to light from the light emitter 42 so that the practitioner can be assured that sufficient curing of the dental material has occurred.

As another option, the tip section 40 may contain one or more electrical components, in addition to or in place of the control circuit 36, for operation of the solid state light emitter 42. Electrical components contained in the tip section 40 would then be disposed of after use on a single patient. In this manner, it may be possible to provide electrical components that optimize the light output for a particular photocurable material that is included in a pre-assembled kit for a certain patient. For example, those components could include a timer to activate an audible signal alarm after a time duration that is matched to an optimal time duration for curing the specific type of photocurable material that is included in the same kit.

Figure 5:
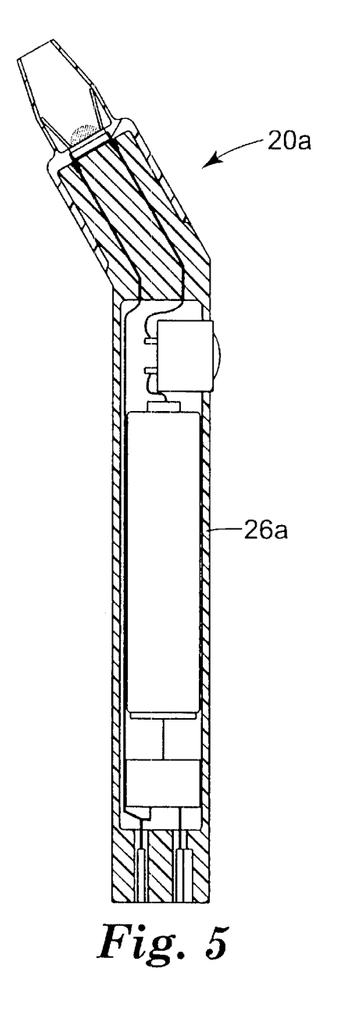
FIG. 5 is a side cross-sectional view of part of a dental light curing apparatus that is constructed in accordance with another embodiment of the invention.

FIG. 5 is an illustration of an apparatus 20a that is constructed in accordance with another embodiment of the invention. The apparatus 20a is essentially the same as the apparatus 20 described above, except for the differences as set out in the paragraphs that follow.

The apparatus 20a includes a housing 26a with a longitudinal axis. A forward portion of the longitudinal axis extends at an angle other than zero relative to a rear portion of the longitudinal axis. As a consequence, the housing 26a has an angled overall appearance. As an alternative to the somewhat sharp angular appearance that is shown in FIG. 5, the longitudinal axis of the housing 26a could instead be curved.

The angled configuration of the housing 26a may be an advantage in certain instances, such as in instances where access to the photocurable material in the oral cavity is somewhat limited. The angled housing 26a may be a particular advantage when attempting to cure photocurable dental material in posterior regions of the patient's oral cavity.

Although not shown in FIG. 5, the apparatus 20a also includes a charging stand that is identical to the charging stand 22. Other aspects, features and methods of operation are identical to the apparatus 20 mentioned above.

Figure 6:
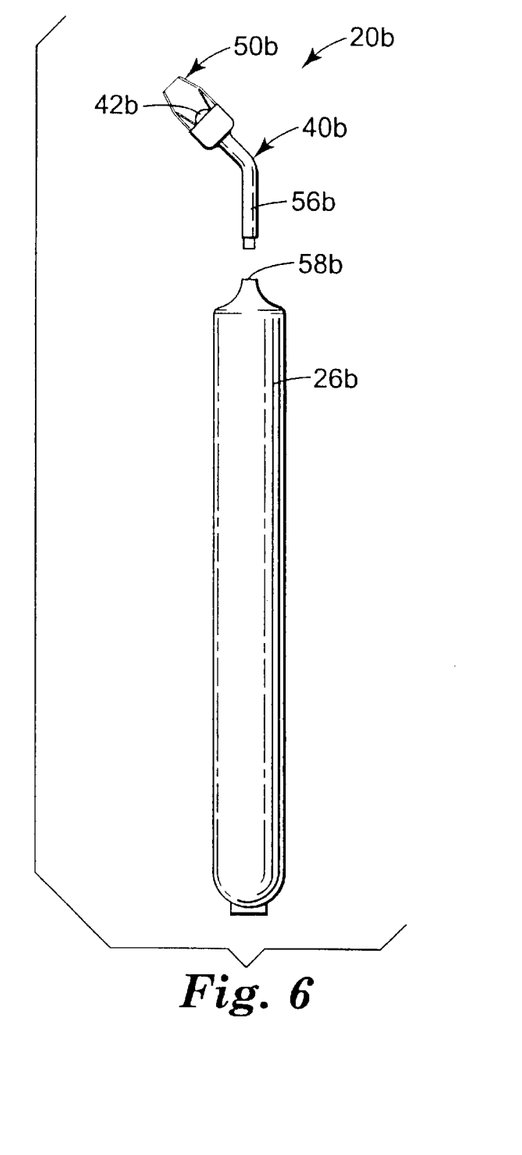
FIG. 6 is a side elevational view in exploded format illustrating part of a dental light curing apparatus that is constructed in accordance with another embodiment of the invention.

An apparatus 20b according to another embodiment of the invention is illustrated in FIG. 6. The apparatus 20b includes a charging stand that is not shown, but is essentially the same as the charging stand 22 described above. The apparatus 20b also includes a housing 26b that is removably received in the charging stand.

The housing 26b preferably contains a control circuit, switch and battery that are essentially identical to the control circuit 36, the switch 38 and the battery 34 respectively. The apparatus 20b also includes a neck section 56b that is detachably connected to the housing 26b. The neck section 56b is part of a tip section 40b and the tip section 40b carries a solid state light emitter 42b.

Preferably, the solid state light emitter 42b is the same as the light emitter 42 described above. Additionally, the tip section 40b includes a light guide 50b which is preferably the same as the light guide 50 described above.

Figure 7:
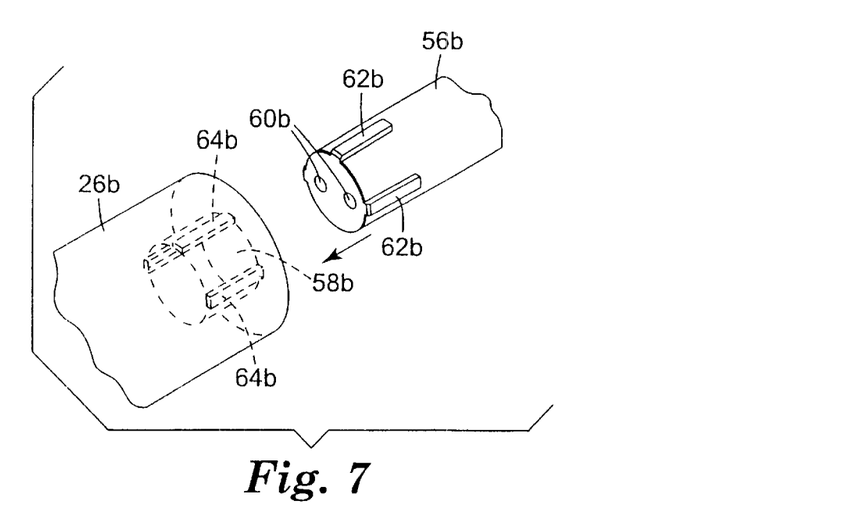
FIG. 7 is a fragmentary, enlarged perspective view of a detachable coupling between a tip section and a housing of the dental light curing apparatus shown in FIG. 6.

FIG. 7 is an enlarged illustration of a rear portion of the neck section 56b as well as a front portion of the housing 26b. As indicated by the arrows, the neck section 56b is slidably received in a socket 58bof the housing 26b in order to mechanically connect the neck section 56b to the housing 26b.

The rear portion of the neck section 56b includes a pair of electrical contacts 60b that are in the shape of raised protrusions. However, other shapes are also possible. The contacts 60b engage respective, mating electrical contacts (not shown) that are located in the socket 58bwhenever the neck section 56b is received in the socket 58b. The contacts including the contacts 60b provide an electrical pathway for current from the battery within the housing 26b to the solid state light emitter 42b whenever the neck section 56b is received in the socket 58b.

Preferably, the neck section 56b and the housing 26b include orienting structure that ensures that the contacts including the contacts 60b are correctly coupled together when the neck section 56b is received in the socket 58b, so that the electrical current provided to the light emitter 42b has proper polarity. In the embodiment illustrated in FIGS. 6 and 7, the orienting means comprises three keys 62b that are provided on a sidewall of the rear portion of the neck section 56b, as well as three mating keyways 64b that are provided on a sidewall of the socket 58b. The keys 62b and keyways 64b ensure that the neck section 56b is in a proper rotative orientation relative to the orientation of the housing 26b whenever the neck section 56b is received in the socket 58b.

As shown in FIG. 7, the keys 62b have identical shapes and the keyways 64b also have identical shapes. Proper rotative orientation of the neck section 56b relative to the housing 26b is assured so long as the keys 62b and keyways 64b are not spaced an equal distance apart. However, other constructions are also possible. An alternative construction is illustrated in FIG. 8.

Figure 8:
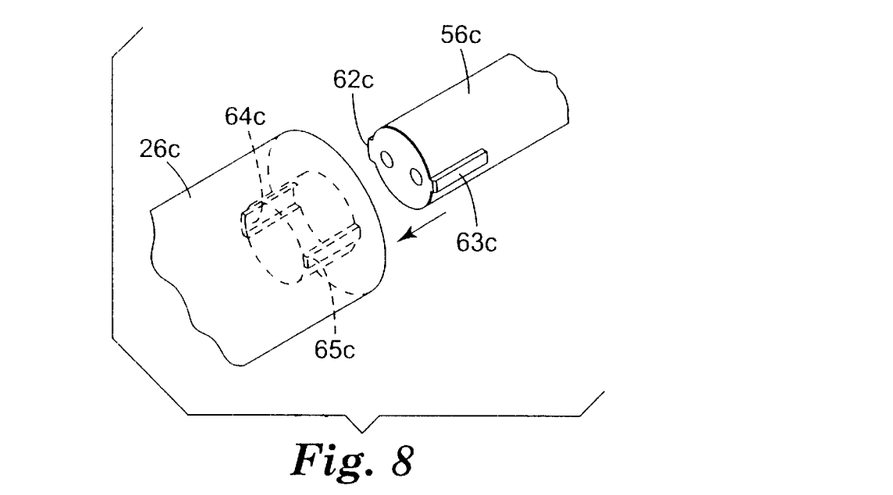
FIG. 8 is a view somewhat similar to FIG. 7, showing another embodiment of the invention.

In the embodiment shown in FIG. 8, key 62c is somewhat wider than key 63c. Additionally, keyway 64c is somewhat wider than keyway 65c. As such, key 62c can only be received in keyway 64c, and proper rotative orientation of the neck section 56b relative to the housing 26b is assured.

As other alternatives, the neck section in the housing may have only one key and keyway. As a further alternative, the electrical contacts (such as contacts 60b) may be associated with or form part of the keys. A variety of other constructions are possible as well.

Figure 9:
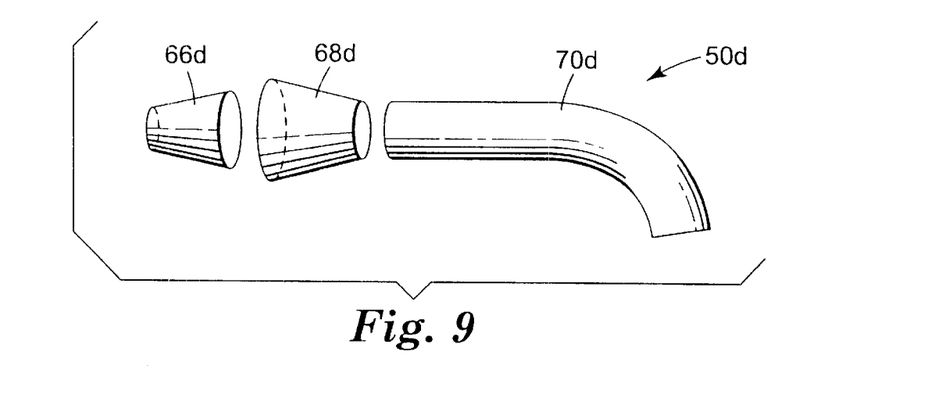
FIG. 9 is a perspective view in exploded format showing a light guide for a dental light curing apparatus that is constructed in accordance with still another embodiment of the invention.

FIG. 9 is an exploded illustration of a light guide 50d that may be used in place of any of the light guides described above. The light guide 50d includes a first element with a first optical surface 66d having a generally conical configuration. The light guide 50d also includes a second element with a second optical surface 68d that also has a generally conical configuration. Preferably, the central axis of the conical configuration for the first optical surface 66d is collinear with a central reference axis of the conical configuration of the second optical surface 68d.

Moreover, the generally conical configuration of the second optical surface 68d is oppositely oriented relative to the generally conical configuration of the first optical surface 66d. Preferably, the smaller end of the conical, first optical surface 66d surrounds a light emitter such as light emitter 42. In addition, the optical surfaces 66d, 68d preferably contact each other so that no gap is presented between the surfaces 66d, 68d.

The light guide 50d also includes a third element with a third optical surface 70d. The third optical surface 70d has a tubular configuration with a generally constant cross-sectional shape for the majority of its length. The cross-sectional shape is preferably circular. An outer, outlet end of the third optical surface 70d can have a circular shape as shown, or alternatively taper to a flattened oval shape, such as the oval shape of the outlet 54 shown in FIG. 4.

Preferably, the third optical surface 70d has a longitudinal axis that is curved along its length, so that a front portion of the third optical surface 70d extends at an angle relative to a rear portion of the third optical surface 70d. Such construction facilitates access to various regions of the oral cavity and is a particular advantage in directing light to posterior regions of the oral cavity.

As an example, the first optical surface 66d may have a conical shape with a cone half angle of 12 degrees and an opening at its rear, smaller portion that is 6.5 mm in diameter. The rear portion is adapted to surround the light emitter. The second optical surface 68d in this example has a cone half angle of 6 degrees, with an output front aperture of 7 mm. Preferably, the rear aperture of the third optical surface 70d fits within the front, output aperture of the second optical surface 68d. Optionally, a substrate surrounds one or more of the optical surfaces 66d, 68d, 70d.

The optical surfaces 66d, 68d, 70d could be constructed of the same material used for the optical surfaces 51, 52 described above. However, as an option, the third element could be made of glass or polymer and have a solid cross-section, or alternatively be made of a bundle of optical fibers.

The light curing apparatus as described in the various embodiments above may be supplied, in whole or in part, within a container that additionally includes dental photo-curable materials and/or dental appliances for a single patient. That assembly consequently forms a kit that can be conveniently manufactured, shipped, and stored in inventory once it arrives in the practitioner's office. The practitioner can then be assured that the items necessary for a particular dental procedure are readily at hand within the container.

Figure 10:
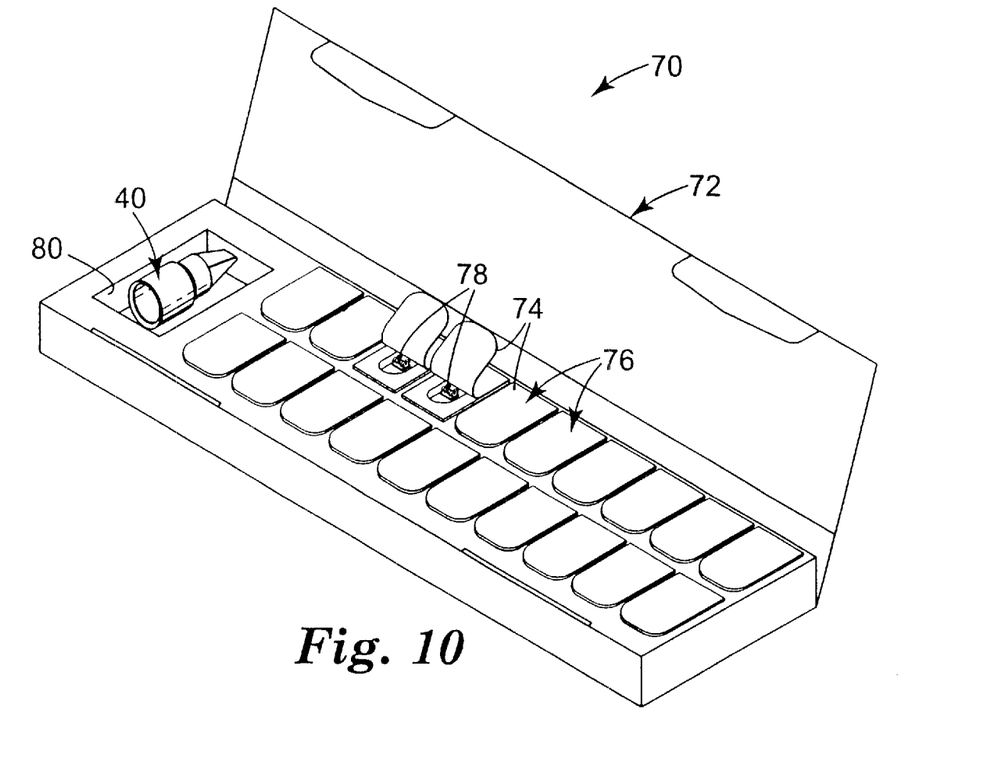
FIG. 10 is a reduced perspective view depicting a dental kit according to yet another embodiment of the invention.

For example, and as illustrated in FIG. 10, a kit 70 comprises an assembly that includes items for a single patient undergoing orthodontic treatment. The kit 70 includes a container 72 that, in this instance, is a rectangular box made of paperboard. The container 72 includes a number of oval-shaped openings (not shown), and a package 76 is received in each opening.

Each of the packages 76 has a lid 74 that may be moved from a closed position to an open position. In FIG. 10, two of the packages are illustrated with lids 74 in an open position. Each of the packages 76 includes a well that contains an orthodontic bracket 78.

Optionally, each bracket 78 is coated with a layer of orthodontic adhesive for bonding the bracket to a tooth. Additional aspects of the container 72, the package 76 and the pre-coated brackets 78 can be found in U.S. Pat. No. 5,328,363, which is incorporated by reference herein. However, the brackets 78 may also be supplied without adhesive, and in that instance the lids 74 may be omitted if desired.

The container 72 also includes a well 80 for receiving the tip section 40. Preferably, the characteristics of the tip section 40, such as the wavelength and lifetime of the solid state emitter 42, are matched to provide optimum results with the particular type of orthodontic adhesive that is pre-coated onto the brackets 78.

Preferably, the brackets 78 are selected by the practitioner to best meet the needs of the patient undergoing treatment. The manufacturer can then ensure that the tip section 40 is constructed to provide optimal results for use with the selected brackets 78 and adhesive.

Furthermore, the kit 70 is an advantage, in that the container 72 contains many of the items necessary for treatment of a particular patient. Advantageously, the tip section 40 can be returned to the container 72 and stored in the container 72 for the duration of treatment after the brackets 78 have been bonded to the teeth, in case the tip section 40 is needed at a later date for use with the same patient. The container 22 including the tip section 40 is then disposed of once the treatment of that patient has been concluded.

Another option is to provide an apparatus similar to the apparatus described above, but without detachable tip sections or light emitters. In this embodiment, the entire apparatus is disposed of after use with a single patient. In such construction, the battery need not be rechargeable, and the entire apparatus could be provided within a kit for a particular patient if desired.

A variety of other constructions are also possible and will be apparent to those skilled in the art. For example, other types of batteries and/or sources of power may be used, such as a power cord for connection with a transformer that is coupled to line power. In addition, an array of two or more solid state light emitters may be provided in place of the single solid state light emitter shown in the drawings. Accordingly, the present invention should not be deemed limited to the specific examples that are described in detail above, but only by a fair scope of the claims that follow along with their equivalents.

What is claimed is:

1. A dental light curing apparatus comprising:
   a housing;
   a solid state light emitter connected to the housing; and
   a source of electrical current detachably connected to the solid state light emitter, wherein the source of electrical current provides a current to the solid state light emitter that is sufficient to reduce the lifetime of the solid state light emitter to less than 10 hours.

2. A dental light curing apparatus according to claim 1 wherein the solid state light emitter is detachably connected to the housing.

3. A dental light curing apparatus according to claim 2 and including a light guide coupled to the solid state light emitter and detachably connected to the housing such that the light guide is detached from the housing simultaneously with detachment of the solid state light emitter from the housing.

4. A dental light curing apparatus according to claim 3 wherein the light guide includes a first optical surface having a generally conical configuration.

5. A dental light curing apparatus according to claim 4 wherein the optical surface comprises an optical stack with a plurality of layers, the layers comprising at least one birefringent polymer and at least one different polymer, wherein a refractive index difference between at least two adjacent layers in a first in-plane direction is greater than or equal to a refractive index difference between the at least two adjacent layers in a second in-plane direction for the film, and further wherein the refractive index difference in the first in-plane direction is greater than a refractive index difference between the at least two adjacent layers in a third out-of-plane direction for the film.

6. A dental light curing apparatus according to claim 2 and including a heat sink connected to the housing, wherein the solid state light emitter is thermally coupled to the heat sink when the solid state light emitter is connected to the housing, and wherein the solid state light emitter detaches from the heat sink simultaneously with detachment of the solid state light emitter from the housing.

7. A dental light curing apparatus according to claim 6 wherein the light guide includes a first optical surface having a generally conical configuration.

8. A dental light curing apparatus according to claim 1 and including a light guide having a first optical surface adjacent the solid state emitter, wherein the first optical surface has a generally conical configuration.

9. A dental light curing apparatus according to claim 8 wherein the light guide also includes a second optical surface adjacent the first optical surface, wherein the second optical surface has a generally conical configuration, wherein the first optical surface and the second optical surface each have respective central reference axes that are substantially colinear, and wherein the generally conical configuration of the second optical surface is oppositely oriented relative to the generally conical configuration of the first optical surface.

10. A dental light curing apparatus according to claim 9 wherein the light guide includes an optical element having a generally cylindrical configuration with first and second ends, and wherein the first end is optically coupled to the second optical surface.

11. A dental light curing apparatus according to claim 10 wherein at least one of the optical surfaces comprises an optical stack with a plurality of layers, the layers comprising at least one birefringent polymer and at least one different polymer, wherein a refractive index difference between at least two adjacent layers in a first in-plane direction is greater than or equal to a refractive index difference between the at least two adjacent layers in a second in-plane direction for the film, and further wherein the refractive index difference in the first in-plane direction is greater than a refractive index difference between the at least two adjacent layers in a third out-of-plane direction for the film.

12. A dental light curing apparatus according to claim 1 and including a light guide comprising a tubular body having first and second ends, wherein the first end is optically coupled to the solid state light emitter.

13. A dental light curing apparatus according to claim 12 wherein the tubular body includes an optical surface that comprises an optical stack with a plurality of layers, the layers comprising at least one birefringent polymer and at least one different polymer, wherein a refractive index difference between at least two adjacent layers in a first in-plane direction is greater than or equal to a refractive index difference between the at least two adjacent layers in a second in-plane direction for the film, and further wherein the refractive index difference in the first in-plane direction is greater than a refractive index difference between the at least two adjacent layers in a third out-of-plane direction for the film.

14. A dental light curing apparatus according to claim 12 wherein at least a portion of the light guide has a generally cylindrical configuration.

15. A dental light curing apparatus according to claim 12 wherein at least a portion of the light guide has a generally conical configuration.

16. A dental light curing apparatus according to claim 1 wherein the solid state light emitter is detachably connected to the housing, and including at least one key and keyway associated with the solid state light emitter and the housing for aligning the solid state light emitter in a certain orientation relative to the housing when the solid state light emitter is connected to the housing.

17. A dental light curing apparatus according to claim 1 wherein the housing has a longitudinal axis with a front portion and a rear portion, and wherein the front portion extends at an angle other than zero degrees relative to the rear portion.

18. A dental light curing apparatus according to claim 1 wherein the source of electrical current provides a current to the solid state light emitter that is sufficient to avoid reducing the lifetime of the solid state light emitter to less than about 2 minutes.

19. A dental light curing apparatus according to claim 1 wherein the source of electrical current provides a current to the solid state light emitter that enables the solid state light emitter to have a lifetime in the range of about 2 minutes to about 2 hours.

20. The method of bonding a quantity of photocurable dental material to a tooth comprising the acts of:

placing a quantity of photocurable material in contact with the tooth; and activating a solid state light emitter in order to direct actinic radiation toward the photocurable material, wherein the act of activating a solid state light emitter includes the acts of directing an electrical current to the solid state light emitter in an amount sufficient to reduce the lifetime of the solid state light emitter to less than 10 hours.

21. A method of bonding a quantity of photocurable dental material to a tooth according to claim 20 and including the act of moving a dental appliance relative to the tooth in order to position the photocurable material between the tooth and the dental appliance.

22. A method of bonding a quantity of photocurable dental material to a tooth according to claim 21 wherein the act of moving a dental appliance relative to the tooth includes the act of shifting the dental appliance as needed with respect to the tooth in order to align the appliance to a desired reference axis of the tooth.

23. A method of bonding a quantity of photocurable dental material to a tooth according to claim 21 wherein the dental appliance is an orthodontic bracket, and wherein the photocurable material is an adhesive.

24. A method of bonding a quantity of photocurable dental material to a tooth according to claim 21 wherein the dental appliance is a veneer, and wherein the photocurable material is an adhesive.

25. A method of bonding a quantity of photocurable dental material to a tooth according to claim 20 wherein the photocurable material is a restorative material.

26. A method of bonding a quantity of photocurable dental material to a tooth according to claim 20 wherein the photocurable material is a sealant.

27. A method of bonding a quantity of photocurable dental material to a tooth according to claim 20 and including the act of providing a light guide for directing the actinic radiation.

28. A method of bonding a quantity of photocurable dental material to a tooth according to claim 27 wherein the light guide includes at least one optical surface that comprises an optical stack having a plurality of layers, the layers comprising at least one birefringent polymer and at least one different polymer, wherein a refractive index difference between at least two adjacent layers in a first in-plane direction is greater than or equal to a refractive index difference between the at least two adjacent layers in a second in-plane direction for the film, and further wherein the refractive index difference in the first in-plane direction is greater than a refractive index difference between the at least two adjacent layers in a third out-of-plane direction for the film.

29. A method of bonding a quantity of photocurable dental material to a tooth according to claim 20 wherein the act of directing an electrical current to the solid state emitter is carried out with an amount sufficient to reduce the lifetime of the solid state light emitter to less than 2 hours.

30. A method of bonding a quantity of photocurable dental material to a tooth according to claim 20 wherein the act of directing an electrical current to the solid state emitter is carried out with an amount sufficient to reduce the lifetime of the solid state light emitter to less than 1 hour.

31. A method of bonding a quantity of photocurable dental material to a tooth according to claim 20 wherein the act of directing an electrical current to the solid state emitter is carried out with an amount that enables the lifetime of the solid state emitter to be within the range of about 2 minutes to about 1 hour.

* * * * *

UNITED STATES PATENT AND TRADEMARK OFFICE
CERTIFICATE OF CORRECTION

PATENT NO.    : 6,419,483 B1   Page 1 of 1
DATED         : July 16, 2002
INVENTOR(S)   : Adam, Randall E.

It is certified that error appears in the above-identified patent and that said Letters Patent is hereby corrected as shown below:

<u>Title page, Item [54] and Column 1, line 1,</u>
Delete "CURLING" and insert in place thereof -- CURING --.

<u>Title page,</u>
Item [56], References Cited, FOREIGN PATENT DOCUMENTS, delete "WO   WO 99/2267  5/1999" and insert in place thereof -- WO   WO 99/22667  5/1999 --; and delete "WO   WO 99/07043   2/2000" and insert in place thereof -- WO   WO 00/07043  2/2000 --.

Signed and Sealed this

Eighteenth Day of February, 2003

JAMES E. ROGAN
*Director of the United States Patent and Trademark Office*